United States Patent [19]

Lee

[11] 4,108,765

[45] Aug. 22, 1978

[54] MEMBRANE SEPARATION OF METHANOL FROM FORMALDEHYDE AQUEOUS MIXTURES

[75] Inventor: Cheng H. Lee, Creve Couer, Mo.

[73] Assignee: Monsanto Company, St. Louis, Mo.

[21] Appl. No.: 849,748

[22] Filed: Nov. 9, 1977

Related U.S. Application Data

[63] Continuation of Ser. No. 636,396, Dec. 1, 1975, abandoned.

[51] Int. Cl.$^2$ ............................................. B01D 13/00
[52] U.S. Cl. ............................... 210/23 R; 210/23 F; 210/500 M
[58] Field of Search .................. 210/23, 321, 500 M; 55/16

[56] References Cited

U.S. PATENT DOCUMENTS

| | | | |
|---|---|---|---|
| 2,981,680 | 4/1961 | Binning | 55/16 X |
| 3,931,000 | 1/1976 | Hamilton | 210/22 R |
| 3,950,247 | 4/1976 | Chiang et al. | 210/23 R |
| 3,956,112 | 5/1976 | Lee et al. | 210/321 R |

*Primary Examiner*—Charles N. Hart
*Assistant Examiner*—David R. Sadowski
*Attorney, Agent, or Firm*—Thomas B. Leslie

[57] ABSTRACT

Methanol is separated from formaldehyde aqueous mixtures by contacting the aqueous mixture feed with a first surface of a polymeric membrane selectively permeable to the methanol over the formaldehyde or formaldehyde and water; while maintaining a second and opposite membrane surface at a lower chemical potential than the first membrane surface for the methanol permeating a portion of the methanol into and through the membrane, and withdrawing from the second membrane surface a mixture having a higher total concentration of methanol in relationship to the formaldehyde or formaldehyde and water than in the methanol, formaldehyde aqueous feed mixtures.

12 Claims, No Drawings

MEMBRANE SEPARATION OF METHANOL FROM FORMALDEHYDE AQUEOUS MIXTURES

This is a continuation of application Ser. No. 636,396 filed Dec. 1, 1975 now abandoned.

BACKGROUND OF THE INVENTION

The invention relates to the membrane separation of methanol from formaldehyde and/or formaldehyde aqueous mixtures. In another aspect the invention relates to hydrophobic polymeric membrane separation of methanol from formaldehyde contained in aqueous mixture feedstreams. Yet in another aspect the invention relates to a process for the hydrophobic, polymeric membrane separation of methanol from formaldehyde and water contained in aqueous mixture feedstreams. Still another aspect of the invention relates to a process for the removal of unreacted methanol contained in formaldehyde streams resulting from the process of manufacturing formaldehyde from methanol.

The separation of organic components from aqueous mixtures such as dispersions, emulsions, solutions, and the like has been accomplished by various means, for example, distillation, filtration, solvent extraction and a combination of these and other methods. However, these methods often fail to provide satisfactory separation of the organic components from the aqueous solution without the utilization of multi-unit apparatus or the high energy input required by phase change techniques. Solvent extraction methods frequently result in the exchange of one aqueous organic mixture for another thus presenting the continuing need for the separation of organic components from aqueous solutions thereof. Because of the disadvantage of the existing method for the separation of organic components from aqueous solutions, and/or mixtures, a simple, inexpensive process adaptable for all types of aqueous solutions is highly desirable.

Membrane separation techniques have been utilized to separate mixtures of two or more molecules, for example, aqueous mixtures, mixed hydrocarbons, azeotropic mixtures, and the like. However known separation techniques utilized in the separation of aqueous mixtures frequently are followed by secondary procedures such as distillation. Because of the disadvantage of the existing separation methods which principally involve a substantial energy input of a thermal, chemical, or mechanical nature, a simple membrane separation for separating methanol from formaldehyde or from formaldehyde aqueous solutions is needed.

The growing need for additional sources of water from salt water or from contaminated sources has directed intensive investigations into the separation of water from aqueous mixtures. Substantial improvements have been made in known water separation procedures based on flash evaporation, membrane separation, electrodialytic action, freezing and the like. However, paralleling such needs for additional sources of water is the need for improved recovery procedures concerning organic components contained in aqueous industrial streams, as well as waste streams. In order to achieve an inexpensive separation of organic components from aqueous mixtures, techniques must be developed which require minimum equipment and energy input.

Accordingly an object of this invention is to provide for the selective separation of methanol from formaldehyde and from formaldehyde aqueous streams utilizing polymeric membrane systems. Another object of this invention is to provide membrane pervaporization, liquid-liquid dialysis, or gas to gas separation of methanol from formaldehyde or from formaldehyde aqueous mixtures wherein the process is as quantitative as possible.

SUMMARY OF THE INVENTION

It has been discovered in accordance with the present invention that methanol is effectively separated from formaldehyde aqueous mixtures through polymeric membranes which are selectively permeable to the methanol over formaldehyde. The effective separation system utilizes a lower chemical potential on the permeate side of the membrane than on the feed side of the membrane through chemical and/or physical means.

One essential feature of the invention requires that the polymeric membrane be selectively permeable to the methanol in comparison to formaldehyde. It has also been discovered in accordance with the present invention that methanol is effectively separated from formaldehyde and water when the polymeric membrane has a separation factor for methanol over water of at least about 0.6 or greater. The process according to the invention separates methanol from aqueous mixtures inclusive of formaldehyde through the steps of contacting an aqueous mixture of methanol and formaldehyde with the first surface of a polymeric membrane selectively permeable to the methanol over the formaldehyde or over formaldehyde and water; maintaining a second and opposite membrane surface at a lower chemical potential than the first membrane surface for the methanol; permeating a portion of the methanol into and through the membrane; and withdrawing at the second membrane surface a mixture having a higher total concentration of methanol over formaldehyde or formaldehyde and water than in the methanol-formaldehyde aqueous feed mixture. The lower chemical potential on the permeate side of the membrane can be maintained by vacuum conditions or at least a pressure differential when pervaporization or gas to gas separation systems are required; however when liquid to liquid dialysis systems are required, an optional feature of the invention is the utilization of a solution sink as a chemical means for maintaining the lower chemical potential. The solution sink can be selected from potential solvents for the methanol and/or complexing solutions.

DETAILED DESCRIPTION OF THE INVENTION

The process of the instant invention comprises utilization of polymeric membranes which are selectively permeable to methanol contained in formaldehyde aqueous mixtures and which are substantially impermeable to the other components of the organic aqueous solution, or materials utilized in the solution sink such as complexing solutions or solvents for the methanol, which are in contact with the membrane. The process according to the invention can utilize methanol solvent complexing solutions, or vacuum vapor mode on the permeate side of the membrane for maintaining the lower chemical potential which is an essential feature of the invention. The lower chemical potential provides a force for driving the membrane permeate through the selective polymeric membrane and can result from the solution sink solvent, complexing solution or vacuum vapor mode having capacity for methanol permeate.

Multi-stage operations are feasible as scale-up utilization of the invention since individual stages permit various concentrations and temperatures in order to achieve optimum driving forces.

Continuous processing according to the invention is achievable wherein an aqueous mixture feedstream containing methanol and formaldehyde is passed on one side and in contact with a hydrophobic, polymeric membrane having selectivity for the methanol over the formaldehyde and/or selectivity for the methanol over the formaldehyde and water, while a solution sink or vapor vacuum is in contact with the permeate side of the membrane. The lower chemical potential can be enhanced through the removal of either the methanol enriched solution sink or enriched vapor by physical means to suitable processing which additionally promotes the recycling of solvents or complexing solutions.

For each individual stage the effectiveness of the separation is shown by the separation factor (S.F.). The separation factor (S.F.) is defined as the ratio of the concentration of two substances, A and B, to be separated, divided into the ratio of the concentrations of the corresponding substances in the permeate $$S. F. = (C_a C_b) \text{in permeate}/(C_a/C_b) \text{in permeant}$$

where $C_a$ and $C_b$ are the concentration of the preferentially permeable component and any other component of the mixture or the sum of other components respectively.

In the pervaporization or vapor vacuum embodiment of the invention, the first or feed side of the membrane is usually under a positive pressure, while the second side is under a negative pressure, relative to the atmospheric pressure and less than the vapor pressure of the permeate. Specifically the pervaporization can occur where the second side of the membrane is maintained at a vacuum of about 0.2mm or more of mercury.

The term "chemical potential" is employed herein as described by Olaf A. Hougen and K. M. Watson ("Chemical Process Principles, Part II," John Wiley, New York, 1947). The term is related to the escaping tendency of a substance from any particular phase. For an ideal vapor or gas, this escaping tendency is equal to the partial pressure so that it varies greatly with changes in the total pressure. For a liquid, change in escaping tendency as a function of total pressure is small. The escaping tendency of a liquid always depends upon the temperature and concentration. In the present invention the feed substance is typically a liquid solution and the permeate side of the membrane is maintained such that a vapor or liquid phase exists. A vapor feed may be employed when the mixture to be separated is available in that form from an industrial process or when heat economies are to be effected in multi-stage.

The term "solution sink" for the purposes of this disclosure defines a liquid sweep utilized on the permeate side of the membrane and is inclusive of both selective solvents for methanol and solutions of methanol complexing agents, or both. Suitable selective solvents for methanol used as solution sink can be selected from solvents which permit the total concentration of methanol to be greater on the permeate side than on the feed or permeant side of the membrane. The term "hydrophobic" for the purpose of this invention will be defined as those polymeric separation membranes which have a separation factor of at least about 0.6 or greater for methanol over water when contacted with an aqueous mixture of methanol and formaldehyde.

Hydrophobic, polymeric membranes used in the inventive process are non-porous, that is, free from holes and tears and the like, which destroy the continuity of the membrane surface. Useful hydrophobic membranes according to the invention are comprised of polymeric materials which with the exception of silicones are comprised of organic polymeric materials. The membranes are preferably as thin as possible while permitting sufficient strength and stability for use in the permeation process. Generally separation membranes from about 0.1 to about 15 mils or somewhat more are utilized according to the invention. High rates of permeation can be obtained by the use of the thinner membranes which can be supported with structures such as fine mesh wire, screens, porous metals, porous polymers, and ceramic materials. The hydrophobic membrane may be a simple disk or a sheet of the membrane substance which is suitably mounted in a duct or pipe or mounted in a plate or frame filter press. Other forms of these membranes may also be employed such as hollow tubes or fibers, through or around which the feed is applied or is recirculated with the permeate being removed from the other side of the tube or fiber as an enriched vapor or enriched sweep solution, complex, or enriched gas stream. There are other useful shapes and sizes which are adaptable to commercial installations, which are in accordance with the invention. The membrane polymeric components may be linear, crosslinked, grafted, and vary over a wide range of molecular weights. Also suitable according to the invention are copolymers and polymeric blends. The hydrophobic membrane, of course, must be insoluble in the aqueous feed solution and the various sweep liquid solvents and complexing agents. Membrane insolubility as used herein is taken to include that the membrane material is not substantially soluble or sufficiently weakened by its presence in the sweep solvent or aqueous feed mixture to impart rubbery characteristics which can cause creep or rupture resulting from conditions of use, including use pressure. The organic membrane may be polymers which have been polymerized or treated so that specific end groups are present in the polymeric material. The polymeric membranes whether hydrophobic or not, according to the inventive process may be prepared by any suitable means such as, for example, casting of film or spinning of hollow fibers from a "dope" containing organic polymer and solvent. Such preparations are well-known in the art. An important control of the separation capacity of particular hydrophobic membranes is exercised by the method used to form and solidify the membrane, e.g., casting from a melt into control atmosphere or solution and the various concentrations and temperatures. The art of membrane use is known with substantial literature being available on membrane supports, fluid flow and the like. The present invention is practiced with such conventional apparatus. The membrane must, of course, be sufficiently thin to permit permeation but sufficiently thick so as not to rupture under operating conditions. The membrane according to the invention must be selectively permeable to the methanol contained in the formaldehyde aqueous mixture in comparison to the formaldehyde and/or the formaldehyde and water of the feedstream.

The following exemplary hydrophobic polymeric membranes are suitable according to the process of the invention and are selectively permeable to methanol over formaldehyde and/or over formaldehyde and water contained in the aqueous feed mixtures:

Polyolefins such as polyethylene, poly(1-butene), poly(4-methyl pentene), polypropylene, bis-1,4-polybutadiene, natural rubber, cross-linked polybutadiene, cis-polyisoprene, polysilicone(dimethyl silicone), copolymers of silicone, and silicone carbonates, cellulose-tridecanoate and the like. These exemplary polymeric materials can also be cross-linked, copolymerized, and/or blended as well as other modifications and still be suitable for the hydrophobic membrane use for selectively separating methanol from formaldehyde and/or formaldehyde and water.

The aqueous mixture containing the methanol and formaldehyde may be continuously or intermittently introduced into the polymeric feed zone. The permeated methanol can be removed from the opposite side of the membrane in batch or continuous manner through the use of various sweep forms, vapor complexing solutions or solvent sinks. The rate of introduction of the aqueous mixture feedstream and the removal of the permeate fraction may be adjusted to provide proportions of permeate and permeant fraction. A number of permeation stages may be employed with the permeate and permeant fractions being recycled through various stages. In each permeation zone the membrane may be used in the form of sheets, tubes, hollow fibers, or other structures which preferentially provide a maximum amount of membrane surface while utilizing a minimum volume of space.

The absolute pressure of the feed and the permeate zone may vary considerably. Pressures of from a few millimeters of mercury to as high as 500 to 1,000 psig or higher, can be used according to the invention depending upon the strength of the membrane and the separation required, i.e., a vapor vs. a liquid system or a combination liquid-vapor system. When the permeate zone is under the liquid phase conditions, pressure is generally not an important factor. However, when gas or vapor feed mixture or pervaporization conditions are utilized, higher pressures on the feed zone can result in greater chemical potential and is desirable.

The membrane permeation step is preferably operated under conditions of temperature which can vary over a wide range from about $-20°$ C to about $200°$ C or more depending upon the selection of the aqueous feed mixtures, solution sinks, and the mode of membrane separation. Higher operating temperatures are frequently desirable because of the increased rates of permeation; however, the present invention is also concerned with energy input efficiency and minimum temperature change for the purpose of separating methanol from formaldehyde and/or formaldehyde and water.

To illustrate further the present invention and the advantages obtained therefrom, the following examples are given without limiting or detracting from the general scope of the invention. It is also possible that many changes in the details presented in the examples can be made without departing from the spirit and scope of the invention.

EXAMPLE 1-25

Methanol was removed from aqueous solutions of methanol and formaldehyde utilizing membranes which are selectively permeable to the methanol over formaldehyde under liquid to gas separation conditions. Those membranes which can be classified as hydrophobic according to the definitions of the invention also permitted the selective separation of methanol over formaldehyde and water under pervaporization conditions as in the following table. The results according to Examples 1-25 are presented in the following table wherein olefinic polymeric membranes, polysilicone membranes, polyurethane membranes, and one modified cellulose membrane were utilized according to the invention. Examples 1-25 utilize the aforementioned polymeric membranes under pervaporization conditions which provide the chemical potential gradient. Conditions such as concentration, temperature, rate, separation factor for methanol over formaldehyde, methanol over water, and methanol over formaldehyde and water are provided.

TABLE

Pervaporization Permeation of Methanol/Formaldehyde/Water through Polymeric Membranes at 64° C
(Permeate Collected at <0.1 mm Pressure)

| Ex. | Membranes | Feed Compositions Percentages by Weight | Separation Factor Methanol over Formaldehyde | Separation Factor Methanol over Water | Separation Factor Methanol over Formaldehyde and Water | Rate[a] (gm/hr-11cm$^2$) |
|---|---|---|---|---|---|---|
| 1 | Polyethylene (Density = 0.92) | 37% Formaldehyde, 53% Water, 10% Methanol | 4.0 | 1.4 | 1.89 | 0.005 |
| 2 | Polyethylene (Density = 0.95) | 37% Formaldehyde, 53% Water, 10% Methanol | 5.0 | 1.0 | 1.3 | 0.003 |
| 3 | Polyethylene (Density = 0.97) | 37% Formaldehyde, 53% Water, 10% Methanol | 3.0 | 0.6 | 0.89 | 0.0014 |
| 4 | Poly (1-butene) | 37% Formaldehyde, 53% Water, 10% Methanol | 3.3 | 0.45 | 0.78 | 0.0013 |
| 5 | Poly (4-methylpentene) | 37% Formaldehyde, 53% Water, 10% Methanol | 3.6 | 0.5 | 0.73 | 0.022 |
| 6 | Polypropylene | 4% Methanol, 48% Formaldehyde, 48% Water | 4.0 | 1.0 | 1.92 | 0.002 |
| 7 | Polyethylene (Density = 0.92) | 4% Methanol, 48% Formaldehyde, 48% Water | 4.65 | 1.0 | 1.7 | 0.003 |
| 8 | Polyethylene (Density = 0.95) | 2.87% Methanol, 48.56% Formaldehyde, 48.56% Water | 5.7 | 0.7 | 1.233 | 0.002 |
| 9 | Polyethylene (Density = 0.95) | 10% Methanol, 45% Formaldehyde, 45% | 4.14 | 0.657 | 1.13 | 0.0025 |

TABLE-continued

Pervaporization Permeation of Methanol/Formaldehyde/Water through Polymeric Membranes at 64° C
(Permeate Collected at <0.1 mm Pressure)

| Ex. | Membranes | Feed Compositions Percentages by Weight | Separation Factor Methanol over Formaldehyde | Separation Factor Methanol over Water | Separation Factor Methanol over Formaldehyde and Water | Rate[a] (gm/hr-11cm$^2$) |
|---|---|---|---|---|---|---|
| 10 | Polyethylene (Density = 0.95) | 40% Methanol, 30% Formaldehyde, 30% Water | 2.6 | 0.69 | 1.1 | 0.005 |
| 11 | cis-1,4 Polybutadiene | 2.53% Methanol, 48.57% Formaldehyde, 48.57% Water | 10.44 | 2.2 | 3.6 | 0.080 |
| 12 | cis-1,4-Polybutadiene | 5.5% Methanol, 47.2% Formaldehyde, 47.2% Water | 6.57 | 2.1 | 2.26 | 0.095 |
| 13 | cis-1,4-Polybutadiene | 29.6% Methanol, 35.18% Formaldehyde, 35.18% Water | 1.23 | 0.68 | 1.14 | 0.15 |
| 14 | Natural Rubber | 5% Methanol, 45% Formaldehyde, 50% Water | 4.5 | 1.39 | 2.2 | 0.1 |
| 15 | cis-1,4 Polybutadiene (crosslinked with 1% benzoyl peroxide) | 37% Formaldehyde, 10% Methanol, 53% Water | 4.0 | 2.4 | 2.3 | 0.1 |
| 16 | cis-1,4 Polybutadiene (crosslinked with 0.5% benzoyl peroxide | 37% Formaldehyde, 10% Methanol, 53% Water | 4.0 | 2.2 | 2.8 | 0.15 |
| 17 | cis-1,4 Polybutadiene (crosslinked with 0.23% benzoyl peroxide) | 37% Formaldehyde, 10% Methanol, 53% Water | 4.0 | 1.7 | 2.25 | 0.2 |
| 18 | cis-polyisoprene | 37% Formaldehyde, 10% Methanol, 53% Water | 5.5 | 1.0 | 1.50 | 0.1 |
| 19 | GE4164 (dimethyl silicone) | 48% Formaldehyde, 48% Water, 4% Methanol | 5.3 | 1.8 | 2.76 | 1.4 |
| 20 | RTV 535 Silicone | 48% Formaldehyde, 48% Water, 4% Methanol | 7.56 | 2.7 | 3.97 | 0.33 |
| 21 | GE 213 (Silicone Carbonate) | 48% Formaldehyde, 48% Water, 4% Methanol | 4.4 | 1.3 | 2.67 | 0.2 |
| 22 | Urethane (based on glycol from polypropylene oxide) | 4% Methanol, 42% Formaldehyde 54% Water | 7.02 | 2.17 | 3.11 | 0.6 |
| 23 | Urethane (based on glycol from tetramethylene oxide) | 5% Methanol, 41% Formaldehyde, 54% Water | 4.0 | 1.5 | 2.03 | 0.66 |
| 24 | Tuftane TF 310 (a commercial urethane) | 2.65% Methanol, 40.84% Formaldehyde, 56.5% Water | 2.43 | 0.46 | 0.7 | 0.09 |
| 25 | Cellulose Tridecanoate | 37% Methanol, 10% Water, 53% Formaldehyde | 4.7 | 2.0 | 2.7 | 0.032 |

[a]Rate normalized to 1 mil membrane thickness

What is claimed is:

1. A process for separating methanol from formaldehyde-aqueous mixtures comprising: contacting the aqueous mixtures consisting of water, methanol and formaldehyde with a first surface of a hydrophobic polymeric membrane selectively permeable to the methanol over the formaldehyde selected from the group consisting of polyolefins, polysilicones, polyurethanes and cellulose tri-long-chain alkanoate; maintaining a second and opposite membrane surface at a lower chemical potential for the methanol than the first membrane surface; permeating a portion of the methanol into and through the membrane; and withdrawing at the second membrane surface a mixture having a higher total concentration of methanol in relationship to formaldehyde than the respective methanol to formaldehyde concentrations contained in the aqueous feed mixtures.

2. A process according to claim 1 wherein the methanol mixture withdrawn from the second membrane surface is in the vapor phase.

3. A process according to claim 2 wherein the second membrane surface is maintained at a pressure less than the vapor pressure of the methanol mixture.

4. A process according to claim 1 wherein the methanol mixture withdrawn from the second membrane surface is in the liquid phase.

5. A process according to claim 4 wherein the lower chemical potential is maintained on the second membrane surface by contacting the second membrane surface with a methanol solution sink.

6. A process for separating methanol from aqueous mixtures containing formaldehyde comprising: contacting the aqueous mixtures consisting of water, methanol and formaldehyde with a first surface of a hydrophobic polymeric membrane selectively permeable to the methanol over the formaldehyde, or formaldehyde and water selected from the group consisting of polyolefins, polysilicones, polyurethanes and cellulose tri-long-chain alkanoate; maintaining a second and opposite membrane surface at a lower chemical potential than the first membrane surface for the methanol permeate; permeating a portion of the methanol into and through the membrane and withdrawing at the second membrane surface a methanol enriched mixture having a higher total concentration of methanol in relationship to formaldehyde, or formaldehyde and water than the concentration of methanol to formaldehyde or formaldehyde and water found in the aqueous feed mixtures.

7. A process according to claim 6 wherein the methanol permeate mixture withdrawn from the second membrane surface is in vapor phase.

8. A process according to claim 7 wherein the second membrane surface is maintained at a pressure less than the vapor pressure of the methanol permeate mixture.

9. A process according to claim 6 wherein the methanol permeate mixture withdrawn from the second membrane surface is in the liquid phase.

10. A process according to claim 9 wherein the lower chemical potential is maintained on the second surface by contacting the second membrane surface with a methanol solution sink.

11. A process according to claim 1 wherein the polymeric membrane is a low density polyethylene.

12. A process according to claim 6 wherein the polymeric membrane is a low density polyethylene.

* * * * *